United States Patent [19]

Brown

[11] Patent Number: 4,543,961
[45] Date of Patent: Oct. 1, 1985

[54] DATA TRANSMISSION SYSTEM

[75] Inventor: David C. Brown, Miami, Fla.

[73] Assignee: Cordis Corporation, Miami, Fla.

[21] Appl. No.: 551,121

[22] Filed: Nov. 14, 1983

[51] Int. Cl.⁴ .............................................. A61B 5/02
[52] U.S. Cl. ................... 128/667; 128/675;
  128/748; 128/780; 73/705; 370/3; 455/605;
  250/231 P
[58] Field of Search .............. 128/634, 665–667,
  128/675, 748, 780; 73/705; 250/226, 231 P;
  455/605; 370/3

[56] References Cited
U.S. PATENT DOCUMENTS

| 3,215,135 | 11/1965 | Franke . | |
|---|---|---|---|
| 3,249,195 | 5/1966 | Polanyi . | |
| 3,267,932 | 8/1966 | Valligre | 128/675 |
| 3,437,088 | 4/1969 | Bielinski | 128/780 |
| 3,480,003 | 11/1969 | Crites | 128/780 |
| 3,553,625 | 1/1971 | Stedman | 128/675 |
| 4,030,485 | 6/1977 | Warner | 128/667 |
| 4,355,910 | 10/1982 | Quick et al. | 73/705 |
| 4,356,396 | 10/1982 | Ruell et al. . | |
| 4,362,358 | 12/1982 | Hafle . | |
| 4,368,645 | 1/1983 | Glenn et al. | 73/705 |
| 4,376,890 | 3/1983 | Engstrom et al. . | |
| 4,408,829 | 10/1983 | Fitzgerald, Jr. et al. | 73/705 |

FOREIGN PATENT DOCUMENTS 2263890 7/1973 Fed. Rep. of Germany ...... 128/634

Primary Examiner—Kyle L. Howell
Assistant Examiner—Ruth S. Smith
Attorney, Agent, or Firm—George H. Gerstman

[57] ABSTRACT

A system is provided for transmitting data through an optical fiber. A beam of light is directed into the optical fiber. A plurality of selective wavelength filter-mirrors are interposed adjacent the optical fiber. Each of the filter-mirrors is operable to reflect only a selected color and to transmit other colors. Each of the filter-mirrors moves relative to the optical fiber in response to a variation of a selected parameter, to vary the quantity of light being reflected by the filter-mirror. Variation of different selected parameters causes movement of corresponding selective wavelength filter-mirrors and concomitant reflection of corresponding selected colors. The quantity and color of the light being reflected are detected by a plurality of selective wavelength transmission members. Each of the transmission members is operable to transmit only a selected color. The quantity and color of the light transmitted by each transmission member are sensed. The illustrative embodiment concerns an optical pressure catheter which transmits data utilizing the described system.

34 Claims, 3 Drawing Figures

4,543,961

DATA TRANSMISSION SYSTEM

BACKGROUND OF THE INVENTION

The present invention concerns a novel system for transmitting data, using a multiplexing technique with an optical fiber.

In U.S. Pat. Nos. 3,215,135 and 3,249,105, optical blood pressure catheters are disclosed in which light is transmitted through optical fibers and a pressure-sensitive diaphragm varies the quantity of the light in response to the pressure exerted on the diaphragm. It is desirable to have the ability to sense a number of different pressure parameters using a single catheter. However, in view of the fact that a catheter should have a small diameter, it is advantageous to avoid having a number of optical fibers passing through a single catheter.

I have discovered a novel system and process by which a single optical fiber can be utilized within a catheter, for transmitting a plurality of informational items through the single optical fiber. The optical fiber being divided into a plurality of segments positioned end-to-end. In this manner, a critical care monitoring catheter could be provided in which a physician could monitor, simultaneously, mean right atrial pressure, right ventricular pressure, and pulmonary arterial or wedge pressure. Alternatively, utilizing the system of the present invention, a cardiac catharization catheter could be provided which would give simultaneous pressure measurements across any one or a combination of the valves of the heart. For example, the catheter could monitor the pressure across the aortic valve which measures the pressure gradient between the aorta and the left ventricle. Another example for which the present invention is useful is in connection with simultaneously measuring the pressures on opposite sides of a balloon in an angiographic catheter.

By utilizing an optical fiber to transmit the plurality of information simultaneously, rather than using electrical wiring, the patient is isolated from electric charges. It is to be understood, however, that although the illustrative embodiment of the invention is directed to a multi-information catheter, the system and process of the present invention are applicable to many other environments in which the transmission of data is required.

It is, therefore, an object of the present invention to provide a system for transmitting a plurality of informational items utilizing a single optical fiber.

Another object of the present invention is to provide a wavelength division multiplexing system utilizing an optical fiber, which system is relatively simple in construction and efficient in operation.

A further object of the present invention is to provide an optical pressure catheter that is operable to sense more than one item at a time using a single optical fiber.

Other objects and advantages of the present invention will become apparent as the description proceeds.

SUMMARY OF THE INVENTION

In accordance with the present invention, a system is provided for transmitting data. The system includes an optical fiber and means for directing light into the optical fiber. A plurality of selective wavelength filter-mirrors are interposed between the adjacent ends of the optical fiber segments. Each of the filter-mirrors is operable to reflect only a selected color and to transmit other colors.

Each of the filter-mirrors is movable relative to the optical fiber in response to a variation of a selected parameter, to vary the quantity of light being reflected by the filter-mirror. In this manner, variation of different selected parameters causes movement of corresponding selective wavelength filter-mirrors and concomitant reflection of corresponding selected colors. Means are provided for detecting the quantity and color of the light being reflected, whereby parameter variations are detected.

In the illustrative embodiment, the detecting means comprises a plurality of selected wavelength transmission members for receiving light that has been reflected. Each selected wavelength transmission member is operable to transmit only a selected color. Means are provided for sensing the quantity and color of the light transmitted by each selected wavelength transmission member.

In the illustrative embodiment, a plurality of beam splitters are located intermediate the filter-mirrors and the selected wavelength transmission members. The beam splitters are used for directing the reflected light to the selected wavelength transmission members.

In the illustrative embodiment, the filter-mirrors are positioned relative to the optical fiber in an order of location so that the first one of the filter members to receive the directed light is adapted to reflect the shortest wavelength color and the last one of the filter-mirrors to receive the directed light is adapted to reflect the longest wavelength.

In accordance with the process of the present invention, data is transmitted by directing light through an optical fiber; reflecting the light so directed with filter-mirrors which reflect only a selected color and transmit other colors, to provide selected colors of light each representing a selected parameter; varying the amount of the selected color light to be reflected in response to variations in the quantity of a respective selected parameter; and detecting the color and quantity of the light that is reflected, whereby the respective selected parameter variations are detected.

An optical pressure catheter is provided in accordance with the present invention, comprising a catheter having an optical fiber located therein. Means are provided for directing light into the optical fiber and a plurality of selective wavelength filter-mirrors are interposed adjacent the optical fiber. Each of the filter-mirrors is operable to reflect only a selected color and to transmit other colors. Means are provided for moving each of the filter-mirrors relative to the optical fiber in response to a variation of a selected pressure parameter, to vary the quantity of light being reflected by the filter-mirror. In this manner, variation of different selected pressure parameters causes movement of corresponding selective wavelength filter-mirrors and concomitant reflection of corresponding selected colors. Means are provided for detecting the quantity and color of the light being reflected, so that the pressure parameter variations are detected.

A more detailed explanation of the invention is provided in the following description and claims, and is illustrated in the accompanying drawings.

BRIEF DESCRIPTION OF THE DRAWINGS

FIG. 1 is a schematic circuit diagram of a system for transmitting data, constructed in accordance with the principles of the present invention.

DETAILED DESCRIPTION OF THE ILLUSTRATIVE EMBODIMENT

Figure 2:
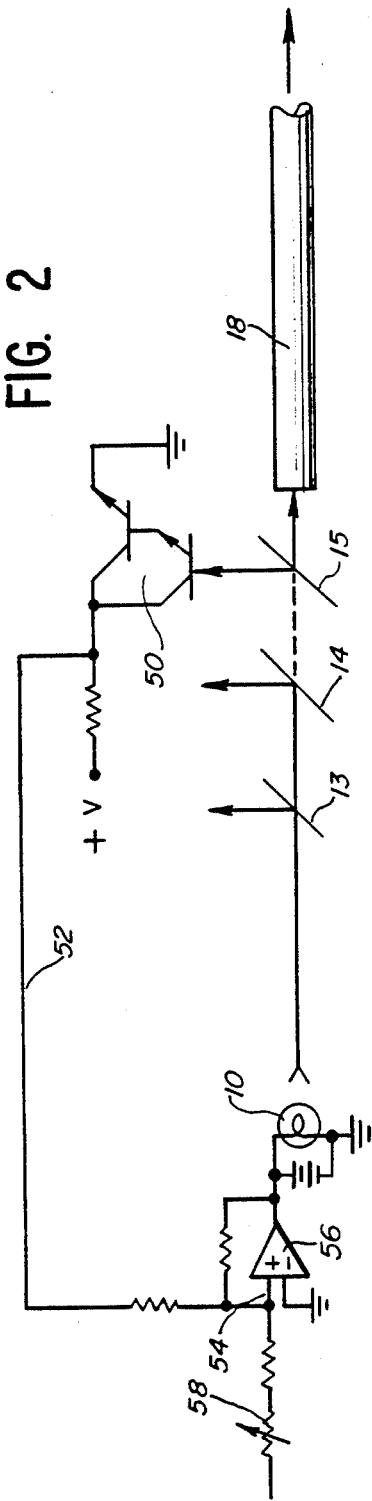
FIG. 2 is a schematic circuit diagram of a system for utilizing some of the light from the data transmission system of FIG. 1, for providing a portion of the energy to the lamp.

Referring to FIG. 1, a tungsten light source 10 emits light which is directed through a condensing lens 11, a collimating lens 12, a beam splitter 13, a beam splitter 14, a beam splitter 15, and a condensing lens 16 to an optical fiber 18. Although three beam splitters 13, 14 and 15 are illustrated, such illustration is only an example and a different number of beam splitters could be utilized.

Beam splitter 13 reflects about 45 percent of the light upwardly, absorbs about 10 percent of the light and about 45 percent of the light is transmitted forwardly. Beam splitter 14 reflects approximately 45 percent of the remaining light upwardly, absorbs about 10 percent of the remaining light and transmits forwardly about 45 percent of the remaining light. Beam splitter 15 reflects about 45 percent of the remaining light upwardly, absorbs about 10 percent and transmits about 45 percent forwardly through condensing lens 16.

Figure 3:
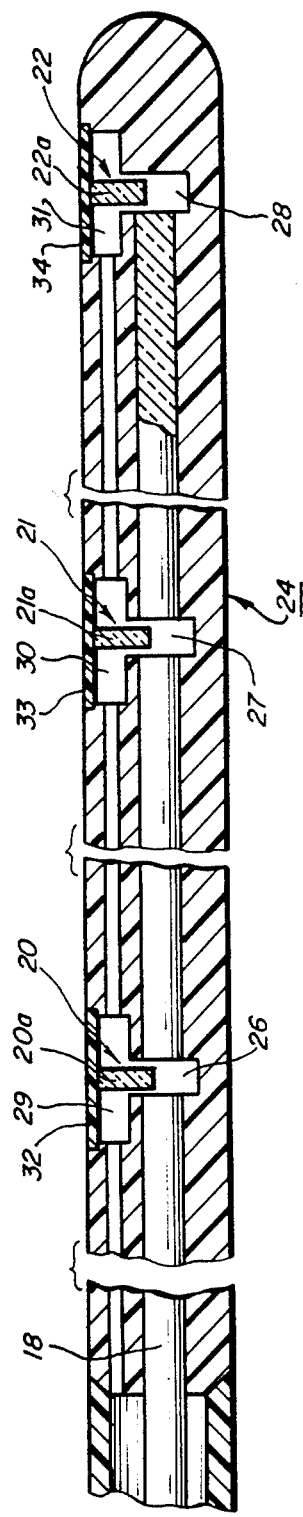
FIG. 3 is an enlarged cross-sectional elevation, partially broken, of the distal end of catheter constructed in accordance with the principles of the present invention.

Although not illustrated in FIG. 1, optical fiber 18 is located within a catheter housing, the details of which are illustrated in FIG. 3, discussed below. A first shutter 20 is interposed adjacent fiber optic 18 for sensing a selected parameter. A second shutter 21 is interposed adjacent fiber optic 18, downstream of shutter 20 for sensing a different parameter. A third shutter 22 is interposed adjacent fiber optic 18, downstream of shutter 21, for sensing a different parameter. Shutters 20, 21 and 22 are wavelength selective shutters and are movable with respect to optical fiber 18 to cause reflection and transmission of selected colors in variable quantities depending upon the quantity of the sensed parameter.

Referring now to FIG. 3, it can be seen that optical fiber 18 is contained within plastic catheter 24. Catheter 24 and optical fiber 18 define vertical openings 26, 27 and 28 which communicate with horizontal openings 29, 30 and 31. Shutters 20, 21 and 22 each comprise a horizontal diaphragm portion 32, 33 and 34, respectively. The peripheral areas of diaphragms 32, 33 and 34 rest on shelves and attached to the underside of the diaphragms are filter-mirrors 20a, 21a and 22a. Filter-mirror 20a transmits yellow light and reflects the other wavelength band (i.e., blue). Filter-mirror 21a transmits magenta light and reflects the other wavelength band (i.e., green). Filter-mirror 22a transmits cyan light and reflects the other wavelength band (i.e., red).

Diaphragms 32, 33 and 34 are each responsive to the sensing of selected pressure parameters. For example, as the pressure sensed by diaphragm 32 is increased, diaphragm 32 will move filter-mirror 20a downwardly to reflect an increasing amount of blue light back through the optical fiber upstream of filter-mirror 20a. Filter-mirror 20a is constructed so that as it is moved a greater distance downwardly, a greater amount of blue light will be reflected.

Likewise, as the pressure is increased upon diaphragm 33, filter-mirror 21a will be urged downwardly to reflect more green light back through the optical fiber that is upstream of filter member 21a. Likewise, as diaphragm 34 senses increased pressure, filter-mirror 22a will be moved further downwardly to reflect more red light back through the optical fiber 18 which is upstream of filter-mirror 22a.

Filter-mirrors 20a, 21a and 22a are dichroic filters which operate by the mechanism of constructive and destructive interference. For this reason they are also known as "interference filters". Dichroic filters are typically constructed by vacuum deposition of thin optical dielectric films on a suitable substrate, such as glass, quartz or plastic. The exact transmission versus reflection characteristic of a particular desired dichroic filter is established by choosing dielectric materials with appropriate indices of refraction, controlling the thicknesses of those films as they are deposited, and by determining both the order of the film layers and the number of those layers. All filters of this type have the attributes of high in-band transmission, high out of band reflection and very small absorption of optical energy.

Referring back to FIG. 1, beam splitters 13, 14 and 15 operate in the same manner in both directions. Thus of the light that is reflected back to beam splitter 15, about 45 percent of the light is reflected downwardly, about 10 percent of the light is absorbed and about 45 percent of the light is transmitted forwardly. Likewise, of the remaining light that is reflected back through the optical fiber, beam splitter 14 directs about 45 percent of the light downwardly, absorbs 10 percent of the light and transmits about 45 percent of the light forwardly to beam splitter 13. Of this remaining light, beam splitter 13 absorbs about 10 percent of the light and reflects about 45 percent of the light downwardly.

A first selected wavelength transmission member 40 is positioned to receive the light that is directed downwardly from beam splitter 15. A second selected wavelength transmission member 41 is positioned to receive the light that is reflected downwardly by beam splitter 14. A third selected wavelength transmission member 42 is positioned to receive the light that is directed downwardly from beam splitter 13. Selected wavelength transmission members 40, 41 and 42 are dichroic filters, similar to filter-mirrors 20a, 21a and 22a but transmit the complementary colors to the colors that are transmitted by the respective filter-mirrors. For example, while filter-mirror 20a transmits yellow light and reflects blue light, selected wavelength transmission member 40 transmits only blue light. Likewise, while filter-mirror 21a transmits magenta light and reflects green light, selected wavelength transmission member 41 transmits only green light. Likewise, while filter-mirror 22a transmits cyan light and reflects red light, selected wavelength transmission member 42 transmits only red light.

The blue light that is transmitted by member 40 is directed to the base of a phototransistor pair 44, comprising a Darlington configuration, with the voltage at output 45 being effectively responsive to the quantity of the pressure sensed by shutter 20. Likewise, the green light transmitted by member 41 impinges upon the base of a transistor pair 46, with the voltage at output 44 being responsive to the pressure sensed by shutter 21. Likewise, the red light transmitted by member 42 impinges upon the base of transistor pair 48, with the voltage at output 49 being responsive to the pressure sensed by shutter 22.

In order to balance the distribution of the spectrum, first filter-mirror 20a (which is closest to lamp 10) reflects the shortest wavelength color (i.e., blue), the second filter-mirror 21a reflects the next highest wavelength color (i.e., green) and the third filter-mirror 22a (which is most distant from lamp 10) reflects the highest wavelength color (i.e., red).

Some of the light emitted by lamp 10 would normally be lost when it reaches beam splitters 13, 14 and 15 and is reflected upwardly. Referring to FIG. 2, a circuit is shown therein for utilizing this light that would normally be lost. To this end, a phototransistor pair 50 is positioned adjacent each of the beam splitters so that the light from lamp 10 that is reflected by the beam splitters upwardly will impinge upon the base of the phototransistor pair, causing a feedback current to be carried via feedback line 52 to the inverting input 54 of an operational amplifier 56. A calibration potentiometer 58 is also connected to inverting input 54, and the output of operational amplifier 56 drives tungsten lamp 10. Although not illustrated in FIG. 2, phototransistor pairs may be utilized for receiving the reflected light from one or all of the beam splitters and for providing a feedback current to the inverting input of the operational amplifier. By using this arrangement, lamp 10 is driven with a constant voltage utilizing energy that might normally be wasted.

Lamp 10, lenses 11, 12 and 16, and beam splitters 13, 14 and 15 are preferably located within a housing which also contains selected wavelength transmission members 40, 41, 42, the detection circuitry and the lamp control circuitry. Catheter 24, with optical fiber 18 therein, is preferably disposable and carries an appropriate connector, not shown, for connecting the catheter to this housing. In FIG. 1 the items to the left of phantom line 60 are within the housing, while the optical fiber 18, shown to the right of phantom line 60, would be part of the disposable catheter.

Although an illustrative embodiment of the invention has been shown and described, it is to be understood that various modifications and substitutions may be made by those skilled in the art without departing from the novel spirit and scope of the present invention.

What is claimed:

1. A system for transmitting data, which comprises:
a plurality of aligned optical fibers positioned end to end;
means for directing light into said optical fibers;
a plurality of selective wavelengths filter-mirror means interposed between the ends of said optical fibers, each of said filter-mirror means being operable to reflect only a selected color and to transmit other colors;
each of said filter-mirror means being movable relative to said optical fibers in response to a variation of a selected parameters, to vary the quantity of light being reflected by said filter-mirror, whereby variation of different selected parameters causes movement of corresponding selective wavelength filter-mirror means and concomitant reflection of corresponding selected colors; and
means for detecting the quantity and color of the light being reflected, whereby parameter variations are detected.

2. A system as described in claim 1, including means for directing the light reflected by the filter-mirror means to said detecting means, said detecting means comprising a plurality of selected wavelength transmission member means for receiving light that has been reflected, with each selected wavelength transmission member means being operable to transmit only a selected color, and means for sensing the quantity and color of the light transmitted by each selected wavelength transmission member means.

3. A system as described in claim 2, said directing means including a plurality of beam splitters located intermediate the filter-mirror means and the selected wavelength transmission means for directing the reflected light to the selected wavelength transmission means.

4. A system as described in claim 1, including means for positioning the filter-mirror means relative to said optical fiber in an order of location so that the first one of said filter-mirror means to receive the directed light is adapted to reflect the shortest wavelength color and the last one of said filter-mirror means is adapted to reflect the longest wavelength color.

5. A system as described in claim 1, including means for using a portion of light that has been lost, for providing a portion of the energy for the light directing means.

6. A system for transmitting data, which comprises:
a plurality of aligned optical fibers positioned end to end;
means for directing light into said optical fibers;
a first selective wavelength filter-mirror means interposed between the ends of two of said optical fibers, said first filter-mirror means being operable to reflect only a first selected color and to transmit other colors;
a second selective wavelength filter-mirror means interposed between the ends of two of said optical fibers, said second filter-mirror means being operable to reflect only a second selected color and to transmit other colors;
a third selective wavelength filter-mirror means interposed between the ends of two of said optical fibers, said third filter-mirror means being operable to reflect only a third selected color and to transmit other colors;
each of said filter-mirror means being movable relative to said optical fibers in response to a variation of a selected parameter, to vary the quantity of light being reflected by said filter-mirror means, whereby variation of different parameters causes movement of corresponding selective wavelength filter-mirror means and concomitant reflection of corresponding selected colors;
means for directing the light reflected by the filter-mirror means to detecting means, said detecting means comprising
a first selected wavelength transmission means for receiving light that has been reflected, with said first selected wavelength transmission means being operable to transmit only the first selected color, and first sensing means for sensing the quantity of the light transmitted by said first selective wavelength transmission means;
a second selected wavelength transmission means for receiving light that has been reflected, with said second selected wavelength transmission means being operable to transmit only the second selected color, and second sensing means for sensing the quantity of the light transmitted by said second selected wavelength transmission means; and a third selected wavelength transmission means for receiving light that has been reflected, with said third selected wavelength transmission means being operable to transmit only the third selected color, and third sensing means for sensing the quantity of the light transmitted by said third selected wavelength transmission means.

7. A system as described in claim 6, said directing means including a plurality of beam splitters located intermediate the filter-mirror means and the selected wavelength transmission means for directing the reflected light to the selected wavelength transmission means.

8. A system as described in claim 6, including means for positioning the filter-mirror means relative to said optical fiber in an order of location so that the closest filter-mirror means to the light directing means is adapted to reflect the shortest wavelength color and the farthest of said filter-mirror means from the light directing means is adapted to reflect the longest wavelength color.

9. A system as described in claim 6, wherein each of said sensing means comprises a photoresponsive semiconductor.

10. A system as described in claim 6, including means for using a portion of light that has been lost for providing a portion of the energy for the light directing means.

11. A system as described in claim 10, said using means comprising photoresponsive means adapted for receiving a portion of the light, and feedback means for conveying output current from said photoresponsive means to aid in energizing the light directing means.

12. A process for transmitting data which comprises the steps of:
  directing light through a plurality of aligned optical fibers positioned end to end;
  reflecting the light so directed with filter-mirror means which reflect only a selected color and transmit other colors, to provide selected colors of light each representing a selected parameter;
  varying the amount of the selected color light to be reflected in response to variations in the quantity of a respective selected parameter; and
  detecting the color and quantity of the light that is reflected, whereby the respective selected parameter variations are detected.

13. A process as described in claim 12, wherein the step of varying comprises moving each of said filter-mirror means relative to the optical fibers in response to variations of the respective selected parameter.

14. A process as described in claim 12, in which the step of detecting comprises providing a plurality of selected wavelength transmission means for receiving light that has been reflected and varied, with each selected wavelength transmission means being operable to transmit only a selected color, and sensing the quantity and color of the light transmitted by each selected wavelength transmission means.

15. A process as described in claim 12, including the step of providing the filter-mirror means in an order of location so that the first one of said filter-mirror means to receive the directed light is adapted to reflect the shortest wavelength color and the last one of said filter-mirror means to receive the directed light is adapted to reflect the longest wavelength color.

16. A process as described in claim 12, including the step of using a portion of light that has been lost, for providing a portion of the energy for the source of the light that is directed through the optical fibers.

17. A process for transmitting data which comprises the steps of:
  directing light through a plurality of aligned optical fibers positioned end to end;
  reflecting the light so directed with filter-mirror means which reflect only a selected color and transmit other colors, to provide selected colors of light, each representing a selected parameter;
  providing the filter-mirror means in an order of location so that the first one of said filter-mirror means to receive the directed light is adapted to reflect the shortest wavelength color and the last one of said filter-mirror means is adapted to reflect the longest wavelength color;
  moving each of said filter-mirror means relative to the optical fibers in response to variations in the quantity of a respective selected parameter;
  directing the light reflected by said filter-mirror means to a plurality of selected wavelength transmission means for receiving light that has been reflected, with each selected wavelength transmission means being operable to transmit only a selected color; and
  sensing the quantity and color of the light transmitted by each selected wavelength transmission means.

18. A process as described in claim 17, including the step of providing a plurality of beam splitters intermediate the filter-mirror means and the selected wavelength transmission means for directing the reflected light to the selected wavelength transmission means.

19. An optical pressure catheter for use in a system for transmitting data, which comprises:
  a catheter having located therein a plurality of aligned optical fibers positioned end to end;
  means for directing light into said optical fibers;
  a plurality of selective wavelength filter-mirror means interposed between the ends of said optical fibers, each of said filter-mirror means being operable to reflect only a selected color and to transmit other colors; and
  means for moving each of said filter-mirror means relative to said optical fibers in response to a variation of a selected pressure parameter, to vary the quantity of light being reflected by said filter-mirror means, whereby variation of different selected pressure parameters causes movement of corresponding selective wavelength filter-mirror means and concomitant reflection of corresponding selected colors.

20. A process for transmitting pressure data by means of a catheter inserted within the body, which comprises the steps of:
  locating within a catheter a plurality of aligned optical fibers positioned end to end;
  directing light through the optical fibers;
  coupling a plurality of filter-mirror means which each reflect only a selected color and transmit other colors, to the locations at which pressures are to be sensed;
  reflecting the light so directed with the filter-mirror means to provide selected colors of light each representing a selected pressure parameter;

varying the amount of the selected color light to be reflected in response to variations in the quantity of a respective selected pressure parameter; and detecting the color and quantity of the light that is reflected, whereby the respective selected pressure parameter variations are detected.

21. A catheter system as described in claim 20, said directing means including a plurality of beam splitters located intermediate the filter-mirror means and the selected wavelength transmission means, for directing the reflected light to the selected wavelength transmission means.

22. A catheter system as described in claim 20, including means for positioning the filter-mirror means relative to said optical fibers in an order of location so that the first one of said filter-mirror means to receive the directed light is adapted to reflect the shortest wavelength color and the last one of said filter-mirror means to receive the directed light is adapted to reflect the longest wavelength color.

23. A catheter system as described in claim 21, including means for using a portion of light that has been lost, for providing a portion of the energy for the light directing means.

24. An optical pressure catheter for transmitting data, which comprises:
a catheter having located therein a plurality of aligned optical fibers positioned end to end;
means for directing light into said optical fibers;
a first selective wavelength filter-mirror means interposed between the ends of two of said optical fibers, said first filter-mirror means being operable to reflect only a first selected color and to transmit other colors;
a second selective wavelength filter-mirror means interposed between the ends of two of said optical fibers, said second filter-mirror means being operable to reflect only a second selected color and to transmit other colors;
a third selective wavelength filter-mirror means interposed between the ends of two of said optical fibers, said third filter-mirror means being operable to reflect only a third selected color and to transmit other colors;
means for moving each of said filter-mirror means relative to said optical fibers relative to said optical fibers in response to a variation of a selected pressure parameter, to vary the quantity of light being reflected by said filter-mirror means, whereby variation of different pressure parameters causes movement of corresponding selective wavelength filter-mirror means and concomitant reflection of corresponding selected colors;
means for directing the light reflected by the filter-mirror means to detecting means, said detector means comprising:
a first selected wavelength transmission means for receiving light that has been reflected, with said first selected wavelength transmission means being operable to transmit only the first selected color, and first sensing means for sensing the quantity of the light transmitted by said first selected wavelength transmission means;
a second selected wavelength transmission means for receiving light that has been reflected, with said second selected wavelength transmission means being operable to transmit only the second selected color, and second sensing means for sensing the quantity of the light transmitted by said second selected wavelength transmission means;
a third selected wavelength transmission means for receiving light that has been reflected, with said third selected wavelength transmission means being operable to transmit only the third selected color, and third sensing means for sensing the quantity of the light transmitted by said third selective wavelength transmission means.

25. A catheter as described in claim 24, said directing means including a plurality of beam splitters located intermediate the filter-mirror means and the selected wavelength transmission means, for directing the reflected light to the selected wavelength transmission means.

26. A catheter as described in claim 24, including means for positioning the filter mirror means relative to said optical fibers in an order of location so that the closest filter-mirror means to the light directing means is adapted to reflect the shortest wavelength color and the farthest of said filter-mirror means from the light directing means is adapted to reflect the longest wavelength color.

27. A catheter as described in claim 24, wherein each of said sensing means comprises a photoresponsive semiconductor.

28. A catheter as described in claim 24, including means for using a portion of light that has been lost, for providing a portion of the energy for the light directing means.

29. A catheter as described in claim 28, said using means comprising photoresponsive means adapted for receiving a portion of the light that has been lost in the optical fibers and feedback means for conveying output current from said photoresponsive means to aid in energizing the light directing means.

30. An optical pressure catheter system for transmitting data, which comprises:
a catheter having located therein a plurality of aligned optical fibers positioned end-to-end;
means for directing light into said optical fibers;
a plurality of selected wavelength filter-mirror means interposed between the ends of said optical fibers, each of said filter-mirror means being operable to reflect only a selected color and to transmit other colors;
means for moving each of said filter-mirror means relative to said optical fibers in response to a variation of a selected pressure parameter, to vary the quantity of light being reflected by said filter-mirror means, whereby variation of different selected pressure parameters causes movement of corresponding selective wavelength filter-mirror means and concomitant reflection of corresponding selected colors;
means for detecting the quantity and color of the light being reflected, whereby pressure parameter variations are detected;
means for directing the light reflected by said filter-mirror means to said detecting means;
said detecting means comprising a plurality of selected wavelength transmission means for receiving light that has been reflected, with each selected wavelength transmission means being operable to transmit only a selected color, and means for sensing the quantity and color of the light transmitted by each selected wavelength transmission means.

31. A process as described in claim 20, wherein the step of varying comprises moving each of said filter-mirror means relative to the optical fibers in response to variations of the respective selected pressure parameter.

32. A process as described in claim 20, in which the step of detecting comprises providing a plurality of selected wavelength transmission means for receiving the light that has been reflected and varied, with each selected wavelength transmission mean being operable to transmit only a selected color, and sensing the quantity and color of the light transmitted by each selected wavelength transmission means.

33. A process as described in claim 20, including the step of providing the filter-mirror means in an order of location so that the closest one of the filter-mirror means to the light source is adapted to reflect the shortest wavelength color and the farthest one of said filter-mirror means from the light source is adapted to reflect the longest wavelength color.

34. A process as described in claim 20, including a step of using a portion of the light that has been lost, for providing energy for the source of the light that is directed through the optical fiber.

* * * * *